Figure 1:
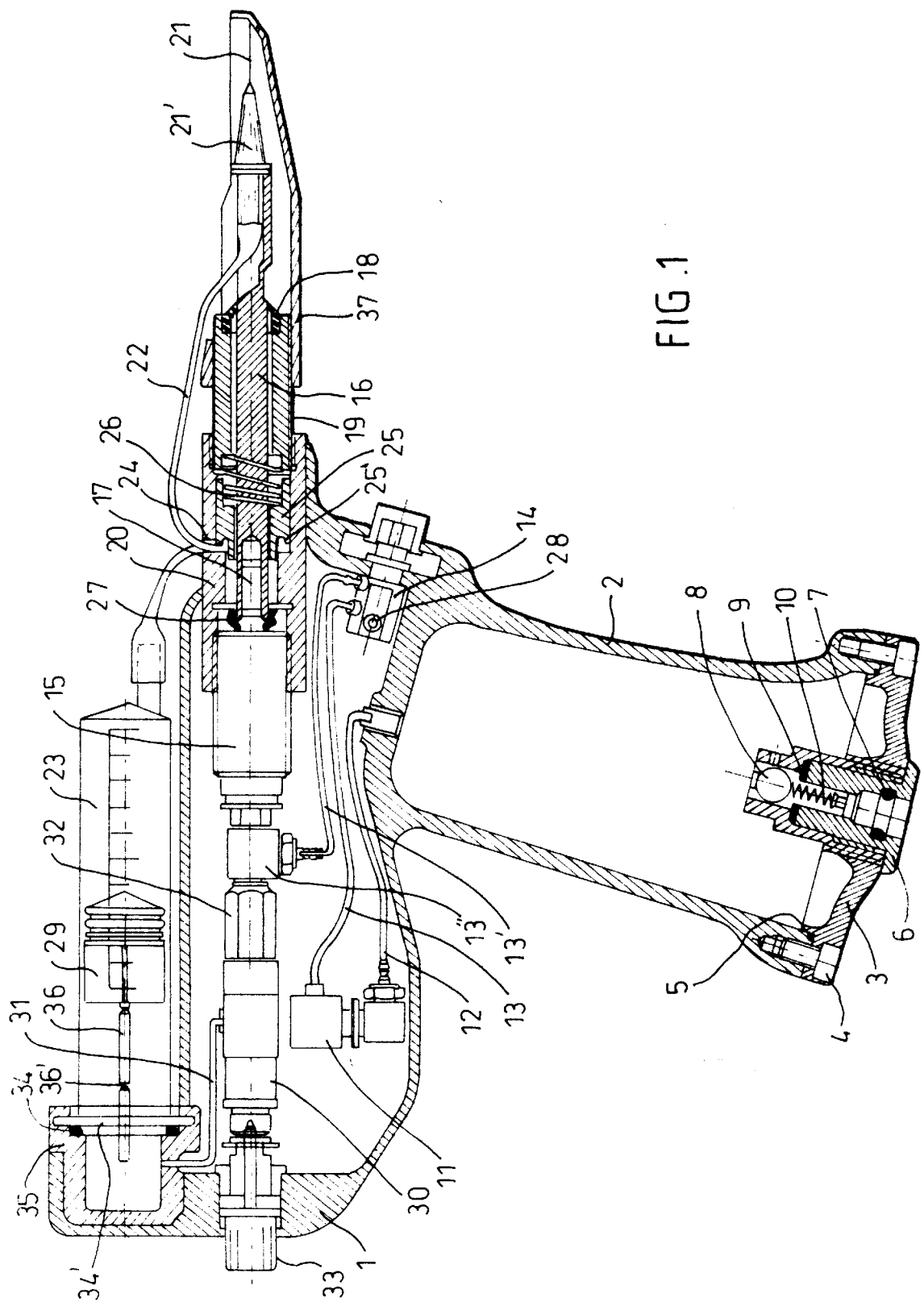

United States Patent

Trapp et al.

[11] Patent Number: 5,833,661
[45] Date of Patent: Nov. 10, 1998

[54] MEDICAL OR VETERINARY INJECTION DEVICE

[75] Inventors: Claude Trapp, Rueil Malmaison; Jean-Pierre Charton, Dijon, both of France

[73] Assignee: MATEF, France

[21] Appl. No.: 307,690

[22] PCT Filed: Mar. 30, 1993

[86] PCT No.: PCT/FR93/00315

§ 371 Date: Sep. 23, 1994

§ 102(e) Date: Sep. 23, 1994

[87] PCT Pub. No.: WO93/19794

PCT Pub. Date: Oct. 14, 1993

[30] Foreign Application Priority Data

Mar. 31, 1992 [FR] France .................................. 92 03870

[51] Int. Cl.⁶ .................................................. A61M 5/20
[52] U.S. Cl. ........................................... 604/147; 604/156
[58] Field of Search .................................. 604/141, 143, 604/156, 146, 147, 150

[56] References Cited

U.S. PATENT DOCUMENTS 3,353,537  11/1967  Knox et al. .............................. 604/143
3,768,472  10/1973  Hodosh et al. .......................... 604/143
4,790,823  12/1988  Charton et al. ......................... 604/157
5,064,413  11/1991  McKinnon, Jr. et al. .............. 604/143
5,173,645  12/1992  Guerrero ................................. 604/150
5,383,851   1/1995  McKinnon, Jr. et al. .............. 604/143
5,780,279   7/1998  Schmidt .................................. 604/143

*Primary Examiner*—Paul J. Hirsch
*Attorney, Agent, or Firm*—William A. Drucker

[57] ABSTRACT

The device includes a handpiece 1, its handle-shaped portion constituting an under pressure air receptacle 2. The handpiece 1 contains a pneumatic jack 15 fed by means of a pressure reducing valve 11 with constant air under pressure derived from the receptacle 2. The jack 15 pushes against a recall spring a catapult 16 bearing an injection needle 21. The piece 1 also bears a movable syringe 23 containing the liquid and connected to the needle 21 by a flexible pipe 22. A piston 29 moving in the syringe 23 is propelled by the air of a pressure chamber 35 fed from the receptacle 2 through a second pressure reducing valve 30. A squeezing piece 25 brings about a flattening of the pipe 22 by prohibiting the flowing of the liquid and it is pushed back at the outlet end of travel of the jack 15 so as to free the pipe 22 from squeezing.

18 Claims, 3 Drawing Sheets

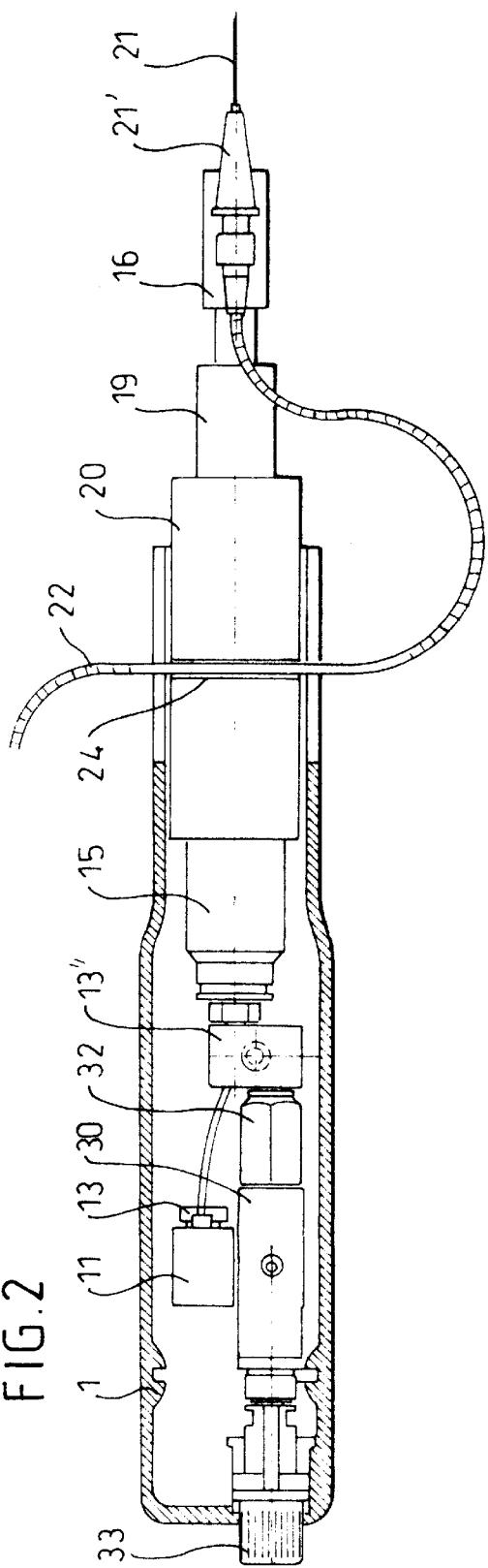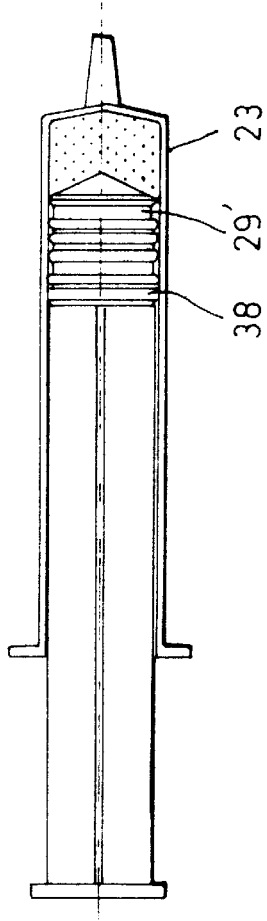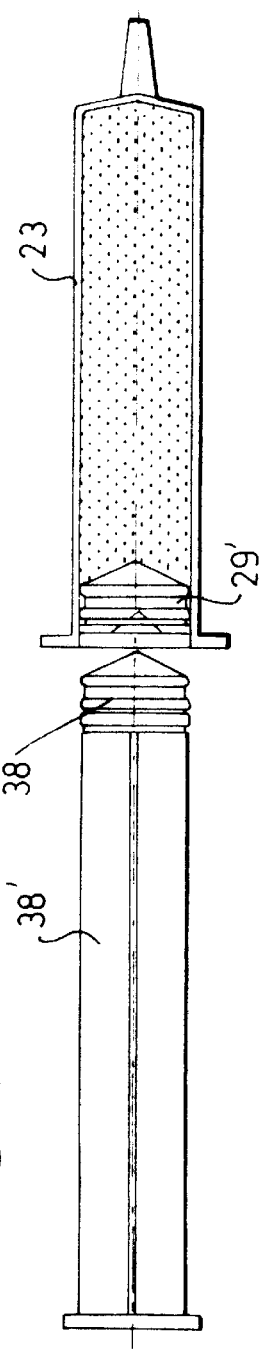

MEDICAL OR VETERINARY INJECTION DEVICE

The invention concerns veterinary or medical devices and more particularly the injection of liquids into living tissues with the aid of a hollow needle which moves the liquid under low pressure as far as its end implanted in the derm or flesh. Another sector concerned is the processing of foodstuffs.

A number of devices have been produced able to replace the hand of the medical practitioner for implanting the needle and injecting the liquid. The purpose of these devices is to prevent the patient from experiencing pain during implantation or injection and avoid the operator from becoming tired. However, up until now, these devices have not been entirely satisfactory as they are too heavy, expensive and inadequately protected against the risks of transmitting infection from one patient to another.

For example, the U.S. Pat. No. 4,790,823 granted 13 Dec. 1988 in the names of CHARTON and GASQUET describes a device comprising a handpiece connected by a flexible pipe to a console placed on the floor, the console providing the handpiece with compressed air or the electric current and even possibly the liquid to be injected under pressure. This liquid originates from a syringe whose piston is propelled by a screw activated by an electric micromotor. However, the console takes up an excessively large amount of space and is expensive, and the handpiece, although light in itself, is connected to it by a compressed air pipe and possibly an electric wire which interferes with its handling.

The French Patent No 78.08827 (published under U.S. Pat. No. 2,401,667) in the name of ISLAND S. R. L., describes a similar device where the piston of the syringe fitted with the needle and borne by the handpiece is propelled by a pneumatic jack fed with compressed gas by a flexible pipe connected by a quick-dismantable connector to a pressure reducing valve which equips an under pressure gas receptacle distinct from the handpiece. Here again, the pipework interferes with the handling of the handpiece which is not autonomous during injections. In addition, the catapult bearing the needle and syringe is quite heavy which requires a relatively high pressure so as to feed the jack and thus requires considerable consumption of compressed air limiting the autonomy of the device. Secondly, the pneumatic jack, which propels the piston of the syringe so as to inject the liquid, receives pressure adjusted by a variable section orifice which makes the speed of injection and thus the volume injected dependent on the manual skill of the operator.

The French Patent No 84.11336 (published under U.S. Pat. No. 2,567,760) in the names of HIBON and KABLA describes an autonomous pistol-shaped handpiece whose handle contains a movable under pressure gas bottle. Here again, the catapult bears the needle and syringe and is again relatively heavy, and secondly the propulsion of the piston of the syringe is ensured by the same jack as that of the catapult which does not allow the injection pressure to be adjusted.

The aim of the present invention is to resolve the drawbacks inherent in known devices and to this effect offers an injection device comprising sufficient autonomy for medical practice allowing for precise and painless implantation and injection and reducing operator fatigue whilst lending itself to rigorous aseptic treatment.

In order to achieve the above, the device of the invention is constituted by a handpiece containing firstly a pneumatic jack designed to propel against a recall spring a catapult bearing an injection needle, and secondly a movable syringe containing the liquid and connected to the needle with in addition a pneumatic member for propelling a mobile piston into the syringe, the jack and pneumatic member being fed by a given receptacle equipped firstly with a pressure reducing valve delivering gas at constant pressure to the jack, and secondly a variable section orifice delivering the under pressure adjustable gas to the pneumatic member, the invention being characterized in that the variable section orifice forms part of a second pressure reducing valve which delivers the gas at stable and adjustable pressure to the pneumatic member, and in that the handpiece contains the receptacle, the pressure reducing valve at constant pressure and the second pressure reducing valve.

The device preferably has the shape of a pistol whose handle constitutes the compressed gas receptacle so as to have the maximum available volume. The compressed air is produced by a small independent connected compressor for filling the receptacle with the aid of a fast connector which may be of any known type.

The device of the invention, according to the information contained in the U.S. Pat. No. 4,790,823 mentioned earlier, again preferably uses a light accurate catapult bearing solely the needle, the latter being connected by a thin flexible tube to a syringe fixed to the handpiece, the needle and syringe unit not being able to be separated and being disposable after use.

So as to reduce to the maximum the weight and spatial requirement of the device, the pneumatic member for propelling the liquid is preferably a pressure chamber to which the syringe is imperviously secured so that the pneumatic pressure directly pushes the piston into the syringe.

Figure 4:
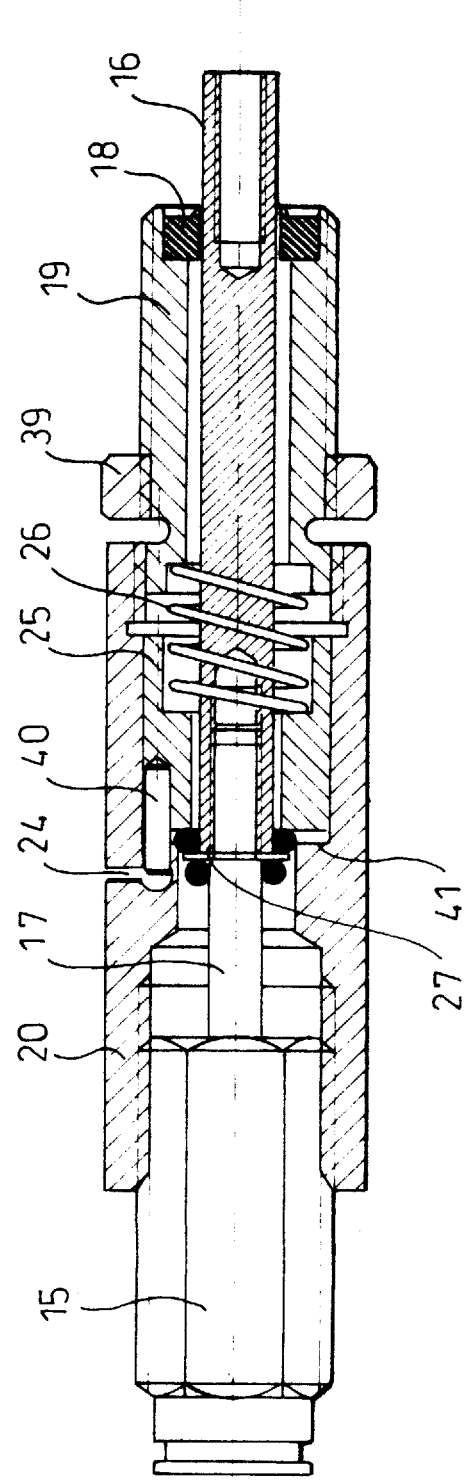

So as to clearly understand the device of the invention, there now follows a non-restrictive example of a preferred embodiment with reference to the accompanying drawing on which:

FIG. 1 is a longitudinal vertical cutaway view of an injection device according to the invention, FIG. 2 is a partial cutaway top view of the device of FIG. 1, FIGS. 3a and 3b are lateral views of a syringe equipped with a free piston and provided with its filling tooling, said piston being shown respectively at the zero graduation of the syringe and at the full filling position of the syringe, and FIG. 4 is an enlarged longitudinal cutaway view of a variant of the squeezing device.

With reference more particularly to FIG. 1, the device of the invention is formed of a handpiece made up of a body 1 extended by a handle 2, the latter forming a receptacle closed by a covering cap 3 held down by screws, such as 4, with a gasket 5.

The covering cap 3 comprises a filling connector 6 with a joint 7 intended to cooperate with a filling tube (not shown) and derived from an air source compressed at 9 bars, for example. The connector 6 is equipped with a nonreturn valve formed of a ball 8 able to be applied by the internal compressed air pressure to a seat 9 via an autoclave effect once the filling tube has been removed. A small spring 10 is provided for pushing back from the outside the ball 8 against any internal pressure lower than a minimum pressure determined by the one below which the functioning of the device would not be satisfactory, such as below 2.5 bars. This then causes the receptacle to be drained, thus indicating the need to refill it.

The body 1 contains a first pressure reducing valve 11 directly connected to the receptacle 2 by a pipe 12 so as to discharge the air at a pressure of 2.5 bars, for example, by a pipe 13. A three-way valve 14 connected to this pipe 13 and opened by activating a push-button sends air via a pipe 13' and a connector 13" into the jack 15 of a catapult 16. The latter is borne by the rod 17 of the jack 15 and by a lip seal 18 embedded at the end of an externally threaded guide 19 screwed into a linking tube 20 secured to the body 1 and bearing the jack 15 at its other end. The jack shown uncut is externally threaded and contains a recall spring. The lip seal 18 prevents the inside of the linking tube 20 from being polluted by oozings of the injection liquid which could fall back along the injection needle 21.

This needle 21 is sealed onto a joining piece 21' kept on an open cradle which extends the catapult 16 and which is relatively elastic so as allow for this holding. Passing through the opening of the cradle is a linking tube 22 secured at one end to the joining piece 21' and at the other end to a graduated syringe 23 containing the liquid to be injected. All these elements are delivered after aseptic treatment and are disposed of after usage without separating them.

The tube 22, known as a catheter, is thin and flexible. The operator, once the needle 21 and the syringe 23 have been installed, makes this tube 22 penetrate into a slit 24 transversally indenting the linking tube 20. Placed inside the latter and around the catapult 16 is a mobile ring 25 which is stressed towards the slit 24 by a spring 26 so that it acts as a squeezing device able to flatten the tube 22 and thus prevent flowing of the liquid to be injected from the syringe 23 to the needle 21. When the jack 15 is activated, a thrustor 27 formed of a washer compacted between the rod 17 and the catapult 16 abuts against the mobile ring 25 by pushing it back against the spring 26. The squeezing of the tube 22 is thus suppressed at the end-of-travel of the catapult 16 which has implanted the needle 21 at the desired location and injection of the liquid then takes place.

When the valve 14 is released, it aerates the jack 15 with fresh air, the latter returning to its retracted position under the action of its internal spring. The mobile ring 25, pushed back by its spring 26, returns to squeeze the tube 22 which stops injection before the needle 21 is removed. At the periphery of its squeezing face, the mobile ring 25 comprises a narrow projection 25' to flatten the tube over a small surface, thus making it possible to reduce the force of the spring 26 and thus the pressure in the jack 15 to the advantage of the autonomy of the device. The thrustor 27 is lined with rubber toroids which dampen the impacts against the mobile ring 25 and against the face of the jack 15 which reduces operating noise.

FIG. 4, which shows a variant of the squeezing device, also shows the jack 15, the linking tube 20 with its slit 24, the mobile ring 25 forming the squeezing element, the spring 26, and the stop 27 fixed at the rod of the jack to which the catapult 16 is screwed, the latter sliding into the joint 18 borne by the guide 19. Here, the ring 25 does not comprise a peripheral flattening projection but is extended by a rod 40. This rod is guided with a small amount of play into a shoulder 41 of the linking tube 20 so as to penetrate into the throat 24 which does not open inside this tube.

The resting of the rod 40 on the catheter previously introduced to the bottom of the slit 24 is then immediate which allows for the use of an even weaker spring and thus less pneumatic pressure in the jack 15.

It shall be noted that the slit 24 preferably comprises an inlet width slightly smaller than the diameter of the catheter which is made to penetrate into it by means of elastic expansion, whereas its bottom is a perforation transverse to the diameter of the catheter which makes it possible to ensure that the latter is in the correct position opposite the rod 40 as it is then able to slide freely inside this perforation.

The bottom of the slit 24 does not open into the bore of the tube 20 so that the slit and catheter remain outside and thus no external pollution can seep inside the mechanism.

The fresh air aerating of the jack 15 may be slowed down by a diaphragm 28 borne by the valve 14 so that the removal of the needle 21 is gradual, thus allowing for a distribution of the liquid along the path. This diaphragm is preferably adjustable by any suitable known device and it may consist, for example, of a check screw traversing the wall of the body 1.

The pressurizing of the liquid to be injected results from a pneumatic member for thrusting on the piston 29 contained in the syringe 23. This member is fed from a connector 13" by a pressure reducing valve 30 discharging with a stable adjustable pressure in a pipe 31. This adjustment depends in particular on the viscosity of the liquid to be injected and is effected by a knurled button 33. A nonreturn valve 32 may possibly be interpositioned.

Instead of using a jack to propel the piston 29, according to the invention, direct thrusting of stable adjustable air derived from the pressure reducing valve 30 is preferably used on this piston. To this effect, the syringe 13 is pressed against a gasket 34 and retained via its small ring 34' against a pressure chamber 35 inserted in the body 1.

FIG. 1 shows an embodiment of a piston 29 adapted to this pneumatic thrusting mode. Instead of a piston rod able to be propelled manually, a thin rod 36 is fixed to the piston so as to solely be used on traction of the piston for filling of the syringe. In addition, this rod 36 comprises embrittlement throats 36' making starts of rupture so as to be divisible close to the small ring 34' of the syringe in order to avoid no reaching the bottom of the capacitor 35. The operator, once the syringe has been filled up to the desired graduation, then breaks this rod 36 and secures the syringe to the capacitor 35. After the injections, the syringe, whose piston 29 has become inaccessible is removed, which avoids the unit (syringe 23, catheter 22 and needle 21) being used again to the advantage of the aseptic treatment of subsequent work interventions.

According to a variant shown on FIGS. 3a and 3b, the piston 29' is free and does not bear any rod. The syringe 23 is delivered with this piston 29' at zero graduation and with a second contiguous piston 38 constituting a disposable tool provided with a traction rod 38' (FIG. 3a). By means of acting on this rod, the two pistons 29' and 38 move towards the opening of the syringe until the tooling piston 38 opens outside the latter. Then the piston 29' is flush with its small ring and the syringe is completely filled and is ready to be secured to the capacitor 35.

It is to be noted that this capacitor 35 is small and much lighter than a jack having the same length as the syringe. Thus, according to one variant (not shown on the drawing), the pressure chamber 35 and thus the syringe 23 could be secured to the catapult 16 without increasing the weight of the mobile unit.

Also shown on FIG. 1 is an element 37 which surrounds and protects the needle 21. This element 21 is scalloped at one end so as to leave the needle 21 visible and guide the operator as regards the penetration point of this needle. The element 37 is screwed via the other end onto the fixed guide 19 which makes it possible to adjust the penetration depth of the needle 21. A counternut 39 shown on FIG. 4 is able to lock this scalloped element 37.

The description given above has been given by way of non-restrictive example and constructive additions or modifications could be made without departing from the context of the invention.

We claim:

1. Liquid injection device constituted by a handpiece (1) containing firstly a pneumatic jack (15) designed to propel against a recall spring a catapult (16) bearing an injection needle (21), and secondly a movable syringe (23) containing the liquid and connected to the needle (21) with in addition a pneumatic member (35) for pushing a mobile piston (29) into the syringe (23), the jack (15) and the pneumatic member (35) being fed by a same receptacle (2) equipped firstly with a pressure reducing valve (11) delivering a gas at constant pressure to the jack (15), and secondly a variable section orifice delivering an adjustable gas under pressure to the pneumatic member (35), wherein the variable section orifice forms part of a second pressure reducing valve (30) which delivers the adjustable gas at stable pressure to the pneumatic member (35) and wherein the handpiece (1) contains the receptacle (2), the pressure reducing valve at constant pressure (11) and the second pressure reducing valve (30).

2. Device according to claim 1, wherein said receptacle (2) constitutes a handle of the handpiece (1).

3. Device according to claim 1, wherein the receptacle (2) comprises an autoclave nonreturn valve (8) which is propelled from outside by a spring (10) which lifts up the valve (8) and drains the receptacle (2) for any internal pressure less than a specific minimum pressure.

4. Device according to claim 1, wherein the handpiece (1) comprises a manual pushbutton valve (14) whose thrust ensures the feeding of the jack (15) for propelling the catapult (16) and whose freeing ensures the fresh air aeration of said jack (15).

5. Device according to claim 4, wherein the fresh air aeration of the thrust jack is effected through a small orifice so as to slow down the return of the needle (21).

6. Device according to claim 1, wherein the catapult (16) is coaxially borne by the pneumatic jack (15) and by an end guide (18) close to the needle (21).

7. Device according claim 1, including a second device for stopping the flowing of the liquid on the connection (22) between the syringe (23) and the needle (21).

8. Device according to claim 7, wherein said connection is a flexible pipe (22), wherein said stopping device comprises a squeezing element (25) with a spring (26) which brings about a flattening of the pipe (22) and wherein an opening pushbutton (27) distances the squeezing element (25) against the spring (26) at the end-of-travel of the catapult (16) propelled by the jack (15).

9. Device according to claim 8, characterized by a transverse slit (24) fitted in a fixed tube (20) surrounding the catapult (16), said fixed tube containing the sliding squeezing element (25) pushed back at the end-of-travel of the pneumatic jack (15) so as to free from squeezing the flexible pipe (22) previously introduced into the slit (24).

10. Device according to claim 9, wherein the squeezing element (25) comprises a narrow peripheral projection (25') for flattening the flexible pipe (22) over a small surface.

11. Device according to claim 8, wherein the squeezing element (25) activates a rod (40) traversing with a small amount of play a fixed tube (20) so as to flatten the pipe (22) outside said tube (20).

12. Device according to claim 1, wherein a nonreturn valve (32) is inserted between the first pressure reducing valve (11) and the pneumatic member (35).

13. Device according to claim 1, wherein the pneumatic member is a pressure chamber (35) cooperating imperviously with a small ring (34') of the syringe (23) so as to directly propel the piston (29) after the syringe (23) filled with liquid has been secured to said chamber.

14. Device according to claim 13, wherein the syringe (23) comprises a piston with a liquid suction rod (36) which has embrittlement throats (36') able to be broken so that the portion of the rod (36) emerging from the syringe can be disposed of once said syringe has been filled and before it has been secured to the pressure chamber (35).

15. Device according to claim 13, wherein the syringe (23) comprises a free piston (29') and wherein its filling is effected via the traction of the rod (38') of a tooling piston (38) contiguous with the free piston (29') and wherein it is removed before the filled syringe is secured to the pressure chamber (35).

16. Device according to claim 1, wherein the syringe (23), the needle (21) and their connection (22) form a fixed disposable unit.

17. Device according to claim 1, wherein a tubular element (37) surrounds and protects the needle (21) when the catapult (16) is inactive, said element (37) being scalloped at one end and fixed at the other end around a guide (19) of the catapult (16).

18. Device according to claim 1, wherein the syringe (23) is borne by the catapult (16) secured to the pressure chamber (35).

* * * * *